United States Patent
Ryll (10) Patent No.: US 6,528,286 B1
(45) Date of Patent: *Mar. 4, 2003

(54) MAMMALIAN CELL CULTURE PROCESS FOR PRODUCING GLYCOPROTEINS

(75) Inventor: Thomas Ryll, San Mateo, CA (US)

(73) Assignee: Genentech, Inc., So. San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/318,911

(22) Filed: May 26, 1999

Related U.S. Application Data (60) Provisional application No. 60/087,291, filed on May 29, 1998.

(51) Int. Cl.[7] ........................... C12N 15/09; C12P 12/00
(52) U.S. Cl. .................... 435/69.7; 435/69.1; 435/70.1; 435/200; 435/358
(58) Field of Search .............................. 435/69.7, 70.1, 435/200, 69.1, 358–362

(56) References Cited

U.S. PATENT DOCUMENTS

| | | |
|---|---|---|
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,096,816 A | 3/1992 | Maiorella |
| 5,122,469 A * | 6/1992 | Mather et al. |
| 5,316,938 A * | 5/1994 | Keen et al. |
| 5,510,261 A | 4/1996 | Goochee et al. |
| 5,523,215 A | 6/1996 | Cousens et al. |
| 5,705,364 A * | 1/1998 | Etcheverry et al. |
| 5,705,964 A | 1/1998 | Tera et al. |
| 5,804,420 A * | 9/1998 | Chan et al. |

FOREIGN PATENT DOCUMENTS

| | | |
|---|---|---|
| DE | 155328 | 6/1982 |
| JP | 2-97379 | 4/1990 |
| JP | 7-23780 | 1/1995 |
| WO | WO 87/00195 | 1/1987 |
| WO | WO 90/03430 | 4/1990 |
| WO | WO 93/10260 | 5/1993 |
| WO | WO 96/39488 | 12/1996 |

OTHER PUBLICATIONS

Albergoni et al., "Response to Heavy Metals in Organisms–I. Excretion and Accumulation of Physiological and Non Physiological Metals in Eugiens Gracilis" *Comp. Biochem. Physiol.* 67C(2):121–127 (1980).

Alexander and Elder, "Carbohydrate dramatically influences Immune reactivity of antisera to viral glycoprotein antigens" *Science* 226(4680):1328–1330 (Dec. 14, 1984).

Anumula, K.R., "Rapid Quantitative Determination of Sialic Acids in Glycoproteins by High–Performance Liquid Chromatography with a Sensitive Fluorescence Detection" *Analytical Biochemistry* 230:24–30 (1995).

Ashkenazi et al., "Protection Against Endotoxic Shock by a Tumor Necrosis Factor Receptor Immunoadhesin" *Proc. Natl. Acad. Sci.* 88:10535–10539 (Dec. 1991).

Ashwell and Harford, "Carbohydrate–specific receptors of the liver" *Annual Review of Biochemistry* 51:531–554 (1982).

Ashwell and Morrell, "The role of surface carbohydrates in the hepatic recognition and transport of circulating glycoproteins" *Advances in Enzymology* 41:99–128 (1974).

Barnes and Sato, "Serum–free cell culture: a unifying approach" *Cell* 22(3):649–655 (Dec. 1980).

Barnes et al., "Methods for Growth of Cultured Cells in Serum–Free Medium" *Analytical Biochemistry* 102:255–270 (1980).

Borys et al., "Ammonia Affects the Glycosylation Patterns of Recombinant Mouse Placental Lactogen–I By Chinese Hamster Ovary Cells in a pH–Dependent Manner" *Biotechnology and Bioengineering* 43(6):505–514.

Borys et al., "Culture pH Affects Expression Rates and Glycosylation of Recombinant Mouse Placental Lactogen Proteins by Chinese Hamster Ovary (CHO) Cells" *Bio/Technology* 11:720–724 (Jun. 1993).

Camakaris et al., "Gene amplification of the Menkes (MNK; ATP7A) P–type ATPase gene of CHO cells is associated with copper resistance and enhanced copper afflux" *Human Molecular Genetics* 4(11):2117–2123 (1995).

Caton et al., "The Antigenic Structure of the Influenza Virus A/PR/8/34 Hemagglutinin (H1 Subtype)" *Cell* 31(2, Pt 1):417–427 (Dec. 1982).

Chotigeat et al., "Role of Environmental Conditions on the Expression Levels, Glycoform Pattern and Levels of Sialyltransferase for hFSH Produced by Recombinant CHO Cells" *Cytotechnology* 15:217–221 (1994).

Cleveland et al., "Routine large–scale production of monoclonal antibodies in a protein–free culture medium" *Journal of Immunological Methods* 56(2):221–234 (Jan. 28, 1983).

Cox et al., "Effect of Media Composition on the Induction of Chorionic Gonadotropin by Sodium Butyrate in HeLa Cells" *In Vitro* 19(1):1–6 (1983).

Fiedler and Simons, "The Role of N–Glycans in the Secretory Pathway" *Cell* 81(3):309–312 (May 5, 1995).

(List continued on next page.)

*Primary Examiner*—David Saunders
(74) *Attorney, Agent, or Firm*—Merchant & Gould P.C.

(57) ABSTRACT

The present invention relates to novel process for the preparation of glycoproteins by mammalian cell culture wherein the sialic acid content of the glycoprotein recovered is optimized by manipulating the cell culture environment. The invention provides for processes in which the sialic acid content of the glycoprotein recovered is increased by addition of copper ion to a cell culture at a concentration effective for stabilization of the sialic acid content.

40 Claims, 7 Drawing Sheets

OTHER PUBLICATIONS

Flack et al., "Site–directed mutagenesis defines the individual roles of the glycosylation sites on follicle–stimulating hormone" *Journal of Biological Chemistry* 269(19):14015–14020 (May 13, 1994).

Gawlitzek et al., "Ammonium Ion and Glucosamine Dependent Increases of Oligosaccharide Complexity in Recombinant Glycoproteins Secreted from Cultivated BHK–21 Cells" *Biotechnology and Bioengineering* 57(5):518–528 (Mar. 5, 1998).

Goochee et al., "The Oligosaccharides of Glycoproteins: Bioprocess Factors Affecting Oligosaccharide Structure and Their Effect on Glycoprotein Properties" *Bio/Technology* 9:1347–1355 (1991).

Gooches et al., "The Oligosaccharides of Glycoproteins: Factors Affectign Their Synthesis and Their Influences on Glycoprotein Properties" *Frontiers in Bioprocessing II*, Todd et al., eds., American Chemical Society pp. 199–240 (1992).

Gramer et al., "Removal of Sialic Acid from a Glycoprotein in CHO Cell Culture Supernatant by Action of and Extracellular CHO Cell Sialidase" *Bio/Technology* 13:692–698 (Jul. 1995).

Ham et al., "Media and Growth Requirements" *Methods in Enzymology* LVIII:44–93 (1979).

Hayter et al., "Glucose–Limited Chemostate Culture of Chinese Hamster Ovary Cells Producing Recombinant Human Interferonγ" *Biotechnology and Bioengineering* 39:327–335 (1992).

Hearing et al., "Isolation of Chinese Hamster Ovary Cell Lines Temperature Conditional for the Cell–Surface Expression of Integral Membrane Glycoproteins" *The Journal of Cell Biology* 108:339–353 (1989).

Helenlus, A., "How N–linked oligosaccharides affect glycoprotein folding in the endoplasmic reticulum" *Molecular Biology of the Cell* 5(3):253–265 (Mar. 1994).

Hu, G., "Copper Stimulates Proliferation of Human Endothelial Cells Under Culture" *Journal of Cellular Biochemistry* 69(3):326–335 (1998).

Hultberg et al., "Copper ions differ from other thiol reactive metal ions in their effects on the concentration and redox status of thiols in HeLa cell cultures" *Toxicology* 117:89–97 (1997).

Kery et al., "Ligand recognition by purified human mannose receptor" *Archives of Biochemistry & Biophysics* 298(1):49–55 (Oct. 1992).

Kimmel et al., "Zinc modulates mononuclear cellular calcitriol metabolism in peritoneal dialysis patients" *Kidney International* 49(5):1407–1412 (1996).

Kobata et al., "Structures and Functions of the Sugar Chains of Glycoproteins" *European Journal of Biochemistry* 209:483–501 (1992).

Kornfeld et al., "Assembly of Asparagine–linked Oligosaccharides" *Ann. Rev. Biochem.* 54:631–664 (1985).

Krishnamurthy et al., "Conditions Promoting Metal–Catalyzed Oxidations during Immobilized Cu–Iminodiacetic Acid Metal Affinity Chromatography" *Biotechnol. Prog.* 11(6):643–650 (1995).

Lanier et al., "Copper Treatment Increases the Production of Recombinant Baculovirus and Extends the Period of Hyperexpression of Polyhedrin and p10" In Vitro (Abstract No. I–15) presented at the World Congress on In Vitro Biology held in San Francisco, CA on Jun. 22–27, 1996) 32(3 Pt II):8A (Mar. 1996).

Le Gros et al., "The Effects of Sodium Butyrate on Lymphokine Production" *Lymphokine Research* 4(3):221–227 (1985).

Miyagi et al., "Differential effect of various inhibitors on four types of rat sialidase" *Glycoconjugate Journal* 10:45–49 (1993).

Mizutani et al., "High Glucose and Hyperosmolarity Increase Platelet–Growth Factor mRNA Levels in Cultured Human Vascular Endothelial Cells" *Biochemical and Biophysical Reseach Communications* 187(2):664–669 (1992).

Munzert et al., "Sialidase Activity in Culture Fluid of Chinese Hamster Ovary Cells during Batch Culture and Its Effect on Recombinant Human Antithrombin III Integrity" *Biotechnology Progress* 12(4):559–563 (Jul. 1996).

Olden et al., "Role of carbohydrates in protein secretion and turnover: effects of tunicamycin on the major cell surface glycoprotein of chick embryo fibroblasts" *Cell* 13(3):461–473 (Mar. 1978).

Parekh, "Effects of Glycosylation on Protein Function" *Current Opinion in Structural Biology* 1:750–754 (1991).

Park et al., "Enhanced β–Galactosidase Production by High Cell–Density Culture of Recombinant Bacillus subtilis with Glucose Concentration Control" *Biotechnology and Bioengineering* 40:686–696 (1992).

Paulson, J., "Glycoproteins: What are the Sugar Chains for?" *TIBS* 14:272–276 (1989).

Rademacher et al., "Glycobiology" *Ann. Rev. Biochem.* 57:785–838 (1988).

Sakai et al., "Growth Inhibition and Heavy Metal Accumulation in Cho Cells" *Cytotechnology* (abstract) 14(suppl. 1),:7.36 (1994).

Scuderi, P., "Differential Effect of Copper and Zinc on Human Peripheral Blood Monocyte Cytokine Secretion" *Cellular Immunology* 126(2):391–405 (1990).

Steinsbach et al., "Effects of Copper on Rat Hepatoma HTC Cells and Primary Cultured Rat Hepatocytes" *Journal of Inorganic Biochemistry* 53:27–48 (1994).

Stockert et al., "The asialoglycoprotein receptor: relationships between structure, function, and expression" *Physiological Reviews* 75(3):591–609 (Jul. 1995).

Varki, "Biological Roles of Oligosaccharides: All of the Theories are Correct" *Glycobiology* 3:97–130.

Warren, L., "The Thiobarbituric Acid Assay of Sialic Acids" *Journal of Biological Chemistry* 234(8):1971–1975 (Aug. 1959).

Wataha et al., "In vitro IL–1β and TNF–α release from THP–1 monocytes in response to metal ions" *Dental Materials* 12(5–6):322–327 (Nov. 1996).

Werner et al., "Mammalian Cell Cultures, Part I: Characterization, morphology and metabolism" *Arzneim.–Forsch./Drug Res.* 43 (II) (10):1134–1139 (1993).

Yao et al., "Direct Determination of Bound Sialic Acids in Sialoglycoproteins by Acidic Ninhydrin Reaction" *Analytical Biochemistry* 179:332–335 (1989).

Yeh et al., "Neuraminidase activity in human leukocytes" *J. of Laboratory Clinical Medicine* 78(5):771–778 (Nov. 1971).

Yohe et al., "Effect of Neurotoxic Divalent Cations on the Activity of the Intrinsic Nerve Ending Membrane–Associated Sialidase of Bovine Brain" *Neurochemical Research* 3:101–113 (1978).

* cited by examiner

MAMMALIAN CELL CULTURE PROCESS FOR PRODUCING GLYCOPROTEINS

This application claims the benefit of U.S. Provisional Application No. 60/087,291, filed May 29, 1998, now abandoned.

FIELD OF THE INVENTION

This invention relates to processes for producing glycoproteins in eukaryotic cell culture. The invention provides cell culture processes which preserve oligosaccharide structures of nascent glycoproteins and greatly facilitate the recovery of glycoproteins containing oligosaccharides terminating in one or more sialic acid residues from the cell culture.

BACKGROUND

Many eukaryotic cell surface- and secreted proteins are post-translationally processed to incorporate N-linked and O-linked carbohydrate (Kornfeld and Kornfeld (1985) Annu. Rev. Biochem. 54:631–64; Rademacher et al., (1988) Annu. Rev. Biochem. 57:785–838). Protein glycosylation is thought to subserve a variety of functions including augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell 81:309–312; Helenius (1994) Mol. Biol. of the Cell 5:253–265; Olden et al., (1978) Cell, 13:461–473; Caton et al., (1982) Cell 37:417–427; Alexander and Elder (1984) Science 226:1328–1330; Flack et al. (1994) J. Biol. Chem. 269:14015–14020). In higher organisms, the nature and extent of glycosylation can markedly affect the circulating half-life and bio-availability of secreted proteins by mechanisms involving receptor mediated uptake and clearance (Ashwell and Morrell (1974) Adv. Enzymol. 41:99–128; Ashwell and Harford (1982) Ann. Rev. Biochem. 51:531–54). Receptor systems have been identified that are thought to play a major role in the clearance of serum proteins through recognition of various sugar components of the oligosaccharide on the glycoproteins (Stockert (1995) Physiol. Rev. 75:591–609; Kery et al., (1992) Arch. Biochem. Biophys. 298:49–55). Since the terminal sialic acid component affects absorption, serum half life, and clearance from the serum as well as the physical, chemical and immunogenic properties of the glycoprotein (Parekh, R. B., suira; Varki, A., (1993) Glycobiology 3:97–100; Paulson, J. (1989), TIBS, 14:272–276; Goochee, et al., (1991) Biotechnology 9:1347–1355; Kobata, A, (1992) Eur. J. Biochem. 209:483–501) production strategies which preserve the terminal sialic acid component can advantageously lengthen protein bioavailability and serum half-life.

Much attention has been paid to factors which affect glycosylation during recombinant protein production such as growth mode (adherent or suspension), fetal bovine serum in media formulation, culture density, oxygenation, pH, ammonium concentration, purification schemes and the like (Werner, R. and Noe, W. (1993), Drug Res. 43:1134–1249; Hayter et al., (1992) Biotech. and Bioeng. 39:327–335; Borys et al., (1994) Biotech and Bioeng. 43:505–514; Borys et al., (1993) Bio/Technology 11:720–724; Hearing et al., (1989) J. Cell Biol. 108:339–353; Goochee et al., in Frontiers in Bioprocessing II, Todd et al., eds (1992) American Chemical Society pp.199–240; U.S. Pat. No. 5,096,816; Chotigeat, W., (1994) Cytotech. 15:217–221; Gawlitzek et al., (1998) Biotech. Bioeng. 57:518–528). Several groups have investigated the process parameters that surround the production of recombinant proteins and especially the effect of media composition in various production strategies (Park et al., (1992) Biotech. Bioeng. 40:686–696; Cox and McClure, (1983) In Vitro, 19:1–6; Mizutani et al., (1992) Biochem. Biophys. Res. Comm. 187:664–669; Le Gros et al. , (1985) Lymph. Res. 4(3):221–227). For example U.S. Pat. No. 5,705,364 discloses methods of altering the sialic acid content of a glycoprotein by controlling factors that affect cell productivity, such as the addition of an alkanoic acid to the culture medium, controlling osmolality of the culture medium, and controlling growth temperature.

Another means of affecting sialic acid content of glycoprotein is by controlling the activity of cellular sialidases (U.S. Pat. No. 5,510,261). Sialidases are cytosolic and membrane-associated enzymes that cleave sialic acid from glycosyl moiety of a glycoprotein. The activity of synaptosomal membrane-associated sialidase of bovine brain was inhibited by copper ion at high concentration following pre-saturation in situ (Yohe, H. C. and Rosenberg, A. (1978) Neurochemical Research (1978) 3:101–113). Cytosolic and membrane-associated sialidase I was shown to be inhibited by copper ion at approximately 1 mM concentration in partially purified extracts from rat liver or rat skeletal muscle (Miyagi, T. et al. (1993) Glycoconjugates Journal 10:45–49).

Culture media and additives frequently contain trace elements and metal ions such as copper for optimal cell growth (for example, "Protease Peptone 2 and 3," "Primatone RL" and "Primatone HS", which are commercially available (Sheffield, England; Difco, USA); Japanese Patent No. 93JP-0171420; International Publication No. WO 90/03430; for composition of various media, for example, DMEM and HAM F12 media, see culture media formulations in American Type Culture Collection Catalogue of Cell Lines and Hybridomas, Sixth Edition, 1988, pages 346–349). A serum-free medium containing Zn (5–100 $\mu$M) or Cu (0.1–50 $\mu$M) for growth of vascular endothelial cells was proposed in Japanese Patent No. 247618. Lanier and Volkman reported an increase in yield of baculovirus expression vectors from recombinant baculoviruses generated in insect (lepidopteran) tissue culture in a medium containing 2 mM $CuSO_4$ (Lanier, L. M. and Volkman, L. M. (1996) In Vitro 32(3) Pt.2:8A). Hultberg et al. found that metals increased the amount of glutathion reduced in HeLa cell culture medium and that copper ion also increased the amount of reduced homocysteine in the medium at copper ion concentrations that did not interfere with cell growth (1–100 $\mu$m). (Hultberg, B. et al. (1997) Toxicology 117:89–97). Divalent metal ions such as $Cu^{2+}$ and $Zn^{2+}$ in soluble form at a concentration of 70–120 mg/L have been added to serum and the serum added to cell culture medium to promote cell growth (German Patent No. 155 328).

However, eukaryotic cells, especially mammalian cells such as Chinese hamster ovary (CHO) cells have been shown to be sensitive to $Cu^{2+}$ concentration in culture media (Camakaris et al., (1995) Human Molecular Genetics 4:2117–2123; Steinebach & Wolterbeek (1994) J. Inorganic Biochemistry, 53:27–48; German Patent 155 328; Sakai, Y. et al. (1994) Cytotechnology 14 (Suppl. 1):7–36). CHO-K1 cells were found to exhibit an $LD_{50}$ of 126 $\mu$M $Cu^{2+}$ in copper-supplemented culture medium (Camakaris, J. et al. (1995) Human Molecular Genetics 4:2117–2123).

The present invention provides for processes for producing glycoproteins by mammalian cell culture which maintain the sialic acid component of oligosaccharides of glycoproteins produced.

SUMMARY OF THE INVENTION

The present invention provides processes for producing glycoproteins by eukaryotic cell culture which provide a glycoprotein product containing oligosaccharides terminating in one or more sialic residues. Advantageously, the cell culture processes of the present invention allow for the recovery of a glycoprotein product whose oligosaccharides are not compromised by degradative events associated with standard cell culture procedures. The processes of the present invention overcome the problem of desialylation of a glycoprotein's oligosaccharide side chains that are associated with standard glycoprotein production methods. Advantageously the invention provides economic and commercial benefits through the recovery of greater useful quantities of glycoprotein product.

Accordingly, the invention provides processes for producing glycoproteins by eukaryotic and especially mammalian cell culture comprising culturing a host cell expressing a glycoprotein in the presence of copper ion in a cell culture medium in a concentration effective to minimize the loss of sialic acid. The present invention therefore provides various cell culture processes to preserve particular glycoforms of glycoproteins produced in mammalian cell culture.

The present invention provides, in a particular embodiment, for producing a glycoprotein in mammalian cell culture by adding an effective amount of $Cu^{2+}$ to a culture medium in which cells producing the glycoprotein are grown. According to one aspect of the invention, the concentration of $Cu^{2+}$ is between approximately 50 $\mu$M and 5 mM. Preferably the $Cu^{2+}$ concentration in the medium is between about 0.1 mM and about 2 mM, preferably at least approximately 250 $\mu$M. More preferably the copper ion concentration is in the range of about 0.1 mM to about 1 mM, especially in the range of about 0.1 mM and about 0.5 mM and more preferably at least approximately 350 $\mu$M, and at least approximately 380 $\mu$M. The foregoing parameter is controlled to affect the mature glycoprotein sialic acid content.

In a particular aspect of the invention, the host cells producing the glycoprotein are grown in a serum-free media. Preferably the host cell is a mammalian host cell and preferably Chinese hamster ovary (CHO) cells including, but not limited to CHO K1, CHO pro3−, CHO DG44, CHO DUXB11 and CHO DP12 cells. Other mammalian host cells useful in the method of the invention include, but are not limited to, mouse myeloma cells, NS0, and hybridoma cells, such as mouse hybridoma cells baby, hamster kidney (BHK) cells, COS cells HeLa cells, C127 cells, mouse L cells, 293 cells and Ltk− cells.

In a preferred embodiment, the invention provides for a process for increasing the sialic acid content of the mature glycoprotein recovered from a mammalian host cell culture comprising contacting the cells expressing the glycoprotein with $Cu^{2+}$ in the culture medium at a concentration that inhibits or prevents desialylation in the cell culture medium. Preferably the $Cu^{2+}$ concentration is at least 150 $\mu$M, more preferably at least approximately 380 $\mu$M. Preferably the host cells are CHO cells. According to this aspect of the present invention, culturing the host cell at a concentration of about 380 $\mu$M provides for the recovery of a glycoprotein with an increased sialic acid content.

The invention further provides, in a particular embodiment, for a cell culture process with two or three phases of cell culture. The invention therefore provides a process for controlling the sialic acid content of a glycoprotein produced by mammalian host cell culture comprising the steps of culturing a host cell which expresses the glycoprotein in a growth phase for a period of time and under such conditions that cell growth is maximized. According to this aspect of the present invention, the growth phase is optionally followed by a transition phase in which cell culture parameters for the desired sialic acid content of the mature glycoprotein are selected and engaged. The growth phase or transition phase is followed by a production phase of the cell culture wherein production parameters optionally selected and engaged in the transition phase are maintained and glycoprotein product is produced and harvested. Adding $Cu^{2+}$ to the cell culture medium after the growth phase, during the transition phase or advantageously at the start of the production phase following the transition phase produces a protein with increased amount of sialic acid which is maintained.

DESCRIPTION OF THE DRAWINGS

FIG. 1.

FIG. 3.

FIG. 4.

FIG. 5.

FIG. 6.

FIG. 7.

DETAILED DESCRIPTION OF THE INVENTION

I. Definitions

The carbohydrate moieties of the present invention will be described with reference to commonly used nomenclature for the description of oligosaccharides. A review of carbohydrate chemistry which uses this nomenclature is found in Hubbard and Ivatt (1981) Ann. Rev. Biochem. 50:555–583. This nomenclature includes, for instance, Man, which represents mannose; GlcNAc, which represents 2-N-acetylglucosamine; Gal which represents galactose; and Glc, which represents glucose. Sialic acids (SA's) are described with reference to the shorthand notation NeuNAc, for 5-N-acetylneuraminic acid, and NeuNGc for 5-glycolylneuraminic acid (J. Biol. Chem, 1982 257:3347; J. Biol. Chem., 1982, 257:3352).

As used herein "glycoprotein" refers generally to peptides and proteins having more than about ten amino acids and at least one oligosaccharide side chain. The glycoproteins may be homologous to the host cell, or preferably, they are heterologous, i.e., foreign, to the host cell being utilized, such as a human protein produced by a Chinese hamster ovary cell. Preferably, mammalian glycoproteins (glycoproteins that were originally derived from a mammalian organism) are used, more preferably, those which are directly secreted into the medium. Examples of mammalian glycoproteins include molecules such as cytokines and their receptors, as well as chimeric proteins comprising cytokinxes or their receptors, including, for instance tumor necrosis factor alpha and beta, their receptors (TNFR-1; EP 417,563 published Mar. 20, 1991; and TNFR-2, EP 417,014 published Mar. 20, 1991) and their derivatives, for example, a tumor necrosis factor receptor-immunoglobulin chimera; renin; a growth hormone, including human growth hormone, and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2. TGF-β3, TGF-β4, or TGF-β5; insulin-like growth factor-I and -II (IGF-I and IGF-II); des(1–3) -IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gammna; colony stimulating factors (CSFs), e.g., M-CSF, GM-CSF, and G-CSF; interleukins (TLs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressings regulatory proteins; antibodies; chimeric proteins, such as immunoadhesins (immunoadhesins are described in, for example, U.S. Pat. Nos. 5,116,964, 5,714,147 and 5,336,603 the disclosures of which are hereby incorporated by reference; immunoadhesons include CD4 (Capon et al., (1989) Nature 337:525–531; Traunecker et al, (1989) Nature 339:68–70; and Byrn et al., (1990) Nature 344:667–670); L-selectin or homing receptor (Watson et al., (1990) J. Cell. Biol. 110:2221–2229; and Watson et al., (1991) Nature 349:164–167); CD44 (Aruffo et al., (1990) Cell 61:11303–1313; CD28 and B7 (Linsley et al., (1991) J. Exp. Med. 173:721–730); CTLA-4 (Linsley et al., J. Exp. Med. 174:561–569); CD22 (Stamenkovic et al., Cell 66:1133–1144); TNF receptor (Ashkenazi et al., (1991) Proc. Natl. Acad. Sci. USA 88:10535–10539; Lesslauer et al., (1991) Eur J. Immunol. 27:2883–2886; and Peppel et al., (1991) J. Exp Med. 174:1483–1489); NP receptors (Bennett et al., (1991) J. Biol. Chem. 266:23060–23067; interferon γ receptor (Kurschner et al., (1992) J. Biol. Chem. 267:9354–9360; 4-1BB (Chalupny et al., (1992) PNAS USA 89:10360–10364) and IgE receptor α (Ridgway and Gorman, (1991) J. Cell. Biol. 115, Abstract No. 1448)) and fragments of any of the above-listed polypeptides.

The term "antibody" is used in the broadest sense and specifically covers single monoclonal antibodies (including agonist and antagonist antibodies) and antibody compositions with polyepitopic specificity. The term "antibody" specifically covers monoclonal antibodies (including full length monoclonal antibodies), polyclonal antibodies, multispecific antibodies (e.g., bispecific antibodies), and antibody fragments. Exemplary antibodies within the scope of the present invention include but are not limited to anti-IL-8, St John et al., (1993) Chest 103:932 and International Publication No. WO 95/23865; anti-CD11a, Filcher et al., Blood, 77:249–256, Steppe et al., (1991) Transplant Intl. 4:3–7, and Hourmant et al., (1994) Transplantation 58:377–380; anti-IgE, Presta et al., (1993) J. Immunol. 151:2623–2632, and International Publication No. WO 95/19181; anti-HER2, Carter et al., (1992) Proc. Natl. Acad. Sci. USA 89:4285–4289, and International Publication No. WO 92/20798; anti-VEGF, Jin Kim et al., (1992) Growth Factors, 7:53–64, and International Publication No. WO 96/30046; and anti-CD20, Maloney et al., (1994) Blood, 84:2457–2466, and Liu et al., (1987) J. Immunol., 130:3521–3526.

The terms "cell culture medium" and "culture medium" and "fermentation medium" refer to a nutrient solution used for growing mammalian cells that typically provides at least one component from one or more of the following categories:

1) an energy source, usually in the form of a carbohydrate such as glucose;

2) all essential amino acids, and usually the basic set of twenty amino acids plus cysteine;

3) vitamins and/or other organic compounds required at low concentrations;

4) free fatty acids; and 5) trace elements, where trace elements are defined as inorganic compounds or naturally occurring elements that are typically required at very low concentrations, usually in the micromolar range.

The nutrient solution may optionally be supplemented with one or more components from any of the following categories:
1) hormones and other growth factors as, for example, insulin, transferrin, and epidermal growth factor;
2) salts and buffers as, for example, calcium, magnesium, and phosphate;
3) nucleosides and bases such as, for example, adenosine, thymidine, and hypoxanthine; and
4) protein and tissue hydrolysates.

The cell culture medium is generally "serum free", when the medium is essentially free of serum from any mammalian source (e.g. fetal bovine serum [FBS]). By "essentially free" is meant that the cell culture medium comprises between about 0–5% serum, preferably between about 0–1% serum and most preferably between about 0–0.1% serum.

The term "mammalian host cell", "host cell", "mammalian cell" and the like, refer to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described for example in *Mammalian Cell Culture,* Mather, J. P. ed., Plenum Press, N.Y. (1984), and Barnes and Sato, (1980) Cell, 22:649. Typically, the cells are capable of expressing and secreting large quantities of a particular glycoprotein of interest into the culture medium. Examples of suitable mammalian host cells within the context of the present invention may include Chinese hamster ovary cells, CHO/-DHFR (CHO, Urlaub and Chasin, Proc. Natl. Acad. Sci. USA, 77:4216 (1980)); dp12.CHO cells (EP 307,247 published Mar. 15, 1989); mouse sertoli cells (TM4, Mather, Biol. Reprod., 23:243–251 (1980)); human cervical carcinoma cells (HELA, ATCC CCL 2); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44–68 [1982]); MRC 5 cells; FS4 cells.

Preferred host cells include Chinese hamster ovary cells CHO/-DHFR (CHO, Urlaub and Chasin, Proc. Natl. Acad. Sci. USA, 77:4216 (1980)); dp12.CHO (CHO DP12) cells (EP 307,247 published Mar. 15, 1989); and subclones of CHO cells including but not limited to, CHO K1, CHO pro3⁻, CHO DUXB11 and CHO DG44 cells (Urlaub et al., (1986) Som. Cell Molec. Genet., 12:555–556).

The term "peptone" within the context of the present invention is meant to refer to a media supplement that is essentially hydrolyzed protein. The source of this protein may be animal by-products from slaughter houses, purified gelatin, or plant material. The protein is typically hydrolyzed using acid, heat or various enzyme preparations. Preferred peptone mixtures are, for example, "Protease Peptone 2 and 3," "Primatone RL" and "Primatone HS", both of which are commercially available (Difco, USA; Sheffield, England).

"Growith phase" of the cell culture refers to the period of exponential cell growth (the log phase) where cells are generally rapidly dividing. During this phase, cells are cultured for a period of time, usually between 1–5 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determine to be optimal for cell growth and divisions. During the growth phase, cells are cultured in nutrient medium containing the necessary additives generally at about 30°–40° C., preferably at about 37° C., in a humidified, controlled atmosphere, such that optimal cell growth is achieved for a particular cell line. Cells are maintained in the growth phase for a period of about between one and five days, usually between two to three days.

"Transition phase" of the cell culture refers to the period of time during which culture conditions for the production phase are engaged. During the transition phase environmental factors such as copper ion concentration and temperature are shifted from growth conditions to production conditions.

"Production phase" of the cell culture refers to the period of time during which cell growth has plateaued or is maintained at a near constant level. During the production phase, logarithmic cell growth has ended and protein production is primary. During this period of time the medium is generally supplemented to support continued protein production and to achieve the desired glycoprotein product.

The term "expression" or "expresses" are used herein to refer to transcription and translation occurring within a host cell. The level of expression of a product gene in a host cell may be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3–7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1–18.88 (Cold Spring Harbor Laboratory Press, 1989).

As used herein, the terms "protein", "peptide" and "polypeptide" are used interchangeably to denote an amino acid polymer or a set of two or more interacting or bound amino acid polymers.

II. Cell Culture Procedures

The present inventors have discovered that copper ion (between approximately 50 $\mu$M and 5 mM $Cu^{2+}$) in a glycoprotein-producing eukaryotic host cell culture medium results in a glycoprotein product with increased sialic acid content in the oligosaccharide side chain. Since proteins expressing one or more sialic acid residues per complex oligosaccharide structure may have longer clearance rates in vivo the clearance rate of the glycoprotein produced may be manipulated within broad limits by the overall degree of sialylation of the preparation. The present invention provides for processes for increasing sialylation of a glycoprotein that can be recovered from a eukaryotic and especially a mammalian cell culture.

According to the present invention eukaryotic cells, especially mammalian cells, are cultured to produce a desired glycoprotein product. In choosing a host cell for the production of the glycoprotein within the context of the present invention, it is important to recognize that different host cells have characteristic and specific mechanisms for the translational and post-translational processing and modification (e.g., glycosylation, cleavage) of the proteins expressed. Appropriate cell lines should be chosen to ensure that the desired post translational modifications are possible. Alternatively, host cells can be modified to express a desired gene product required for the specific post-translational modification.

In particular, the mammalian cells that express the desired protein should express or be manipulated to express the particular enzymes such that under the appropriate conditions, described herein, the appropriate post translational modification occurs in vivo. The enzymes include those enzymes necessary for the addition and completion of N- and O- linked carbohydrates such as those described in Hubbard and Ivan suira for N-linked oligosaccharides. The enzymes optionally include oligosaccharyltransferase, alpha-glucosidase I, alpha-glucosidase II, ER alpha(1,2) mannosidase, Golgi alpha-mannodase I, N-acetylyglucosaminyltransferase I, Golgi alpha-mannodase II, N-acetylyglucosaminyltransferase II, alpha (1,6)fucosyltransferase, and β(1,4)galactosyltranferase. Additionally, the host cell expresses the appropriate sialyl transferase that can be expected to attach the terminal sialic acid in specific position and linkage as part of the host cell genome. Optionally, the host cell can be made to express the appropriate sialyl transferases by, for instance, transfection of the host cell with the DNA encoding the sialyl tranferase.

The sialyl transferases described above would be expected to add the terminal sialic acid residue to the appropriate oligosaccharide core structure such as Galβ1-4GlcNAc. Appropriate sialyl transferases within the context of the present invention include, but are not limited to, those sialyl transferases which catalyze the complex sialylation and branching of the N- and O- linked oligosaccharides.

The overall content of sialic acid in the glycoprotein may be affected by controlling cell culture parameters which affect cell specific productivity (see, for example, U.S. Pat. No. 5,705,364). Factors which affect cell specific productivity are well known in the art and include, but are not limited to, factors which affect DNA/RNA copy number, factors which affect RNA, such as factors which stabilize RNA, media nutrients and other supplements, the concentration of transcription enhancers, the osmolality of the culture environment, the temperature and pH of the cell culture, and the like.

For the culture of the mammalian cells expressing the desired protein and capable of adding the desired carbohydrates in specific position and linkage, numerous culture conditions can be used paying particular attention to the host cell being cultured. Suitable culture conditions for mammalian cells are well known in the art (J. Immunol. Methods (1983)56:221–234) or can be easily determined by the skilled artisan (see, for example, *Animal Cell Culture: A Practical Approach* 2nd Ed., Rickwood, D. and Hames, B. D., eds. Oxford University Press, New York (1992)), and vary according to the particular host cell selected.

The mammalian cell culture of the present invention is prepared in a medium suitable for the particular cell; being cultured. Commercially available media such as Ham's F10 (Sigma), Minimal Essential Medium (MEM, Sigma), RPMI-1640 (Sigma), and Dulbecco's Modified Eagle's Medium (DMEM, Sigma) are exemplary nutrient solutions. In addition, any of the media described in Ham and Wallace, (1979) Meth. Enz., 58:44; Barnes and Sato, (1980) Anal. Biochem., 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art.

In a particular embodiment, the mammalian host cell is a CHO cell, preferably a CHO DUX (DHFR-) or subclone thereof such as CHO K1, CHO pro3⁻, CHO DG44, CHO DP12 cell and a suitable medium contains a basal medium component such as a DMEM/HAM F-12 based formulation (for composition of DMEM and HAM F12 media and especially serum free media, see culture media formulations in American Type Culture Collection Catalogue of Cell Lines and Hybridomas, Sixth Edition, 1988, pages 346–349) (the formulations of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Protease Peptone 2 and 3, Primatone HS or Primatone RL (Difco, USA; Sheffield, England), or the equivalent; a cell protective agent, such as Pluronic F68 or the equivalent Pluronic polyol; Gentamycin; and trace elements. Preferably the cell culture media is serum free.

The glycoproteins of the present invention may be produced by growing cells which express the desired protein under a variety of cell culture conditions. For instance, cell culture procedures for the large or small scale production of proteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode.

In a preferred embodiment the cell culture of the present invention is performed in a stirred tank bioreactor system and a fed batch culture procedure is employed. In the preferred fed batch culture the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers, sedimentation, etc. and the culture medium is continuously or intermittently introduced and removed from the culturing vessel).

Further, the cells of the culture may be propagated according to any scheme or routine that may be suitable for the particular host cell and the particular production plan contemplated. Therefore, the present invention contemplates a single step or multiple step culture procedure. In a single step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

According to a preferred aspect of the invention, fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and preferably about 37° C. and a suitable $dO_2$ is between 5–90% of air saturation.

At a particular stage the cells may be used to inoculate a production phase or step of the cell culture. Alternatively, as described above the production phase or step may be continuous with the inoculation or growth phase or step.

According to the present invention, the cell culture environment during the production phase of the cell culture is controlled. According to the process of the present invention, the copper ion concentration in the culture medium is manipulated such that the desired sialic acid content is achieved and maintained in the resulting glycoprotein. In a preferred aspect, the production phase of the cell culture process is preceded by a transition phase of the cell culture in which parameters (such as addition of copper ion) for the production phase of the cell culture are engaged.

According to the present invention the concentration of copper ion is controlled to control desialylation resulting in increased sialic acid in the glycoprotein recovered from the process of the invention. Concentration of copper ion of at least 50 $\mu$M are used and modified according to the particular host cell being cultured and the desired sialic acid content of the glycoprotein produced. In determining the appropriate concentration of the copper ion, reference can be made to FIGS. 2–7 as well as parameters such as cell culture phase and viability as described in the Examples below. According to the invention concentrations of copper ion are chosen keeping in mind other process parameters such as the osmolality of the production phase which can affect the cell specific productivity and sialic acid content of the glycoprotein produced.

The present invention provides, in a particular embodiment, for producing a glycoprotein in mammalian cell culture by adding an effective amount of $Cu^{2+}$ to a culture medium in which cells producing the glycoprotein are maintained. According to one aspect of the invention, a glycoprotein production phase following a growth and optionally a transition phase is employed and the concentration of $Cu^{2+}$ is between approximately 50 $\mu$M and 5 mM. Preferably the $Cu^{2+}$ concentration in the medium is between about 0.1 mM and about 2 mM, preferably at least approximately 250 $\mu$M. More preferably the copper ion concentration is in the range of about 0.1 mM to about 1 mM, especially in the range of about 0.1 mM and about 0.5 mM and more preferably at least approximately 350 $\mu$M, and at least approximately 380 $\mu$M.

Alternatively, for other mammalian host cells and other glycoproteins, small test cultures can be prepared and sialic acid content of the glycoprotein may be ascertained at various copper ion concentrations appropriate for the particular host cell being cultured and the particular phase of the culture. Preferably, the copper ion is added to the host cell culture at or about the time the production phase of the cell culture is initiated. Conveniently, a transition phase is employed during the cell culture process preceding the production phase in which the cell culture conditions as discussed herein are engaged for the desired increase in sialic acid content and hence the desired glycoform profile. At this time the temperature of the culture may also be shifted. Preferably to between about 30° C. and 36° C. and more preferably to about 33° C.

The copper ion is added by any means known in the art, such as by the addition of $CuCl_2$. In a preferred embodiment the copper is added in batch to the fed batch culture system with or without other appropriate nutrients as described herein or known to those skilled in the art of mammalian cell culture.

It will be understood by the skilled artisan that the cell culture procedures of the present invention are selected to achieve the desired level of sialylation of the produced protein. Process parameters in addition to those described herein which influence the degree of sialylation include oxygen level, ammonium level, pH and hexose level. Culture density, time and storage conditions such as temperature also influence sialylation. The present invention is meant to include those process parameters which are additionally most suitable for enhanced sialylation.

III. Recovery of the Glycoprotein

Following the polypeptide production phase, the polypeptide of interest is recovered from the culture medium using techniques which are well established in the art.

The polypeptide of interest preferably is recovered from the culture medium as a secreted polypeptide. For example, as a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

IV. Analysis of the Glycoprotein

The complex carbohydrate portion of the glycoprotein produced by the processes of the present invention may be readily analyzed if desired, by conventional techniques of carbohydrate analysis. Thus, for example, techniques such as lectin blotting, well-known in the art, reveal proportions of terminal mannose or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange or size exclusion chromatography or other methods well-known in the art. The pI of the glycoprotein can also be measured, before and after treatment with neuraminidase to remove sialic acids. An increase in pI following neuraminidase treatment indicates the presence of sialic acids on the glycoprotein.

The resulting carbohydrates can be analyzed by any method known in the art including those methods described herein. Several methods are known in the art for glycosylation analysis and are useful in the context of the present invention. Such methods provide information regarding the identity and the composition of the oligosaccharide attached to the peptide. Methods for carbohydrate analysis useful in the present invention include but are not limited to lectin chromatography; HPAEC-PAD, which uses high pH anion exchange chromatography to separate oligosaccharides based on charge; NMR; Mass spectrometry; HPLC; GPC; monosaccharide compositional analysis; sequential enzymatic digestion.

Sialic acid can be determined separately by the direct calorimetric method of Yao et al. (Anal Biochem. 179:332–335 (1989)) in triplicate samples. In a preferred embodiment the thiobarbaturic acid (TBA) of Warren, L. J. Biol Chem 238:(8) (1959) or the method of Anumula, K. R., (1995) Anal. Biochem. 230:24–30 is used.

Having now generally described the invention, the same will be more readily understood through reference to the following examples which are provided by way of illustration, and are not intended to be limiting of the present invention, unless specified.

EXAMPLES

General Methods

A. Cell Line

The Chinese hamster ovary (CHO)cell line used as the mammalian host cell line was derived from CHO DG44 cells.

B. Construction of Soluble Type 1 TNFR-IgG$_1$ Chimera

A soluble type 1 TNFR-IgG$_1$ chimera was constructed by gene fusion of the extracellular domain of human type 1 TNFR with the hinge region and C$_H$2 and C$_H$3 domains of IgG$_1$ heavy chain (further referred to as TNF1-IgG$_1$) as described in Ashkenazi et al., (1991) Proc. Natl. Acad. Sci. USA 88:10535–10539.

C. Cell Culture

The gene encoding the soluble type 1 TNFR-IgG$_1$ was introduced into CHO DG44 cells by transfection. This was accomplished using the calcium phosphate technique for introducing DNA into mammalian cells. Clones expressing the TNFR1-IgG1 were amplified in methotrexate yielding high expressing clones and subsequently adapted to serum free medium. These cells were under continuous selective pressure until transferred to nonselective medium for growth and expansion of the inoculum.

To provide cells for TNFR1-IgG$_1$ production cultures the cell population described above was expanded from the medium containing methotrexate by serial subcultivations in vessels of increasing volumes to growth medium containing no methotrexate. For these steps of the process the non selective growth medium was DMEM/HAM F-12 based formulation (see, for example, U.S. Pat. No. 5,122,469, herein incorporated by reference in its entirety) with modified concentrations of some components, such as glucose, amino acids, salts, sugar, vitamins glycine, hypoxanthine, and thymidine; recombinant human insulin, hydrolyzed peptone (Protease Peptone 2 or 3, Primatone HS or Primatone RL), a cell protective agent such as Pluronic F68 (pluronic polyol) or the equivalent; Gentamycin; and trace elements.

The cultures were controlled at pH 7.2+/−0.4 by the use of $CO_2$ gas (acid) and /or $Na_2CO_3$ (base). Temperature was controlled near 37° C. during the growth period. Dissolved oxygen was maintained above 5% of air saturation by direct sparging with air and/or oxygen gas.

The growth phase for each culture was followed by a second phase or transition phase wherein culture parameters were changed from growth to production conditions. During this transition phase the temperature of the culture system was decreased, generally to about between 30 and 35° C. and usually about 33° C. Copper chloride was added to the culture medium. Product accumulated during the production phase was analyzed for sialic acid content.

D. Recovery of the TNFR-IgG$_1$

The TNFR1-IgG$_1$ chimera was purified to greater than 95% homogeneity by affinity chromatography on immobilized *Staphylococcus aureus* Protein A as described by Capon et al., supra.

E. Carbohydrate Analysis

Sialic acid content was analyzed by the method of Warren, L. (1959) J. Biol. Chem. 234:1971–1975. or the method of Anumula, K. R. (1995) Anal. Biochem. 230:24–30.

Example I

Glycoprotein production culture was inoculated at 0.2% packed cell volume (PCV). Cells were grown for about 2 days under optimal growth conditions (37° C., low osmolality). When reaching 1% PCV (after about 2 days) the culture conditions were changed from optimal growth to production conditions. This means that growth is slowed under these conditions. This change includes a temperature shift to 33° C. and the addition of a complex feed (a concentrated form of media components).

Results

The cell culture is productive for about 12 days. A harvest on day 9, to insure a desirable sialic acid (SA) content, does result in a significant loss of product concentration as shown in Table I below.

TABLE I

| Culture Scale | Product concentr. on day 9 (mg/l) | Product concentr. on day 12 (mg/l) | % increase in Product concentr. |
|---|---|---|---|
| 2 L | 341 | 509 | 49 |
| 2 L | 344 | 543 | 58 |
| 2 L | 378 | 512 | 35 |
| 1000 L | 272 | 442 | 63 |

Culture scale, product concentrations and % increase between product concentrations on days 9 and 12 for four representative production cultures.

As can be seen in Table I, an about 50% increase in productivity can be achieved when running the culture for 12 days instead of 9 days with comparable product quality if the sialic acid content can be stabilized in the later half of the culture.

Figure 1:
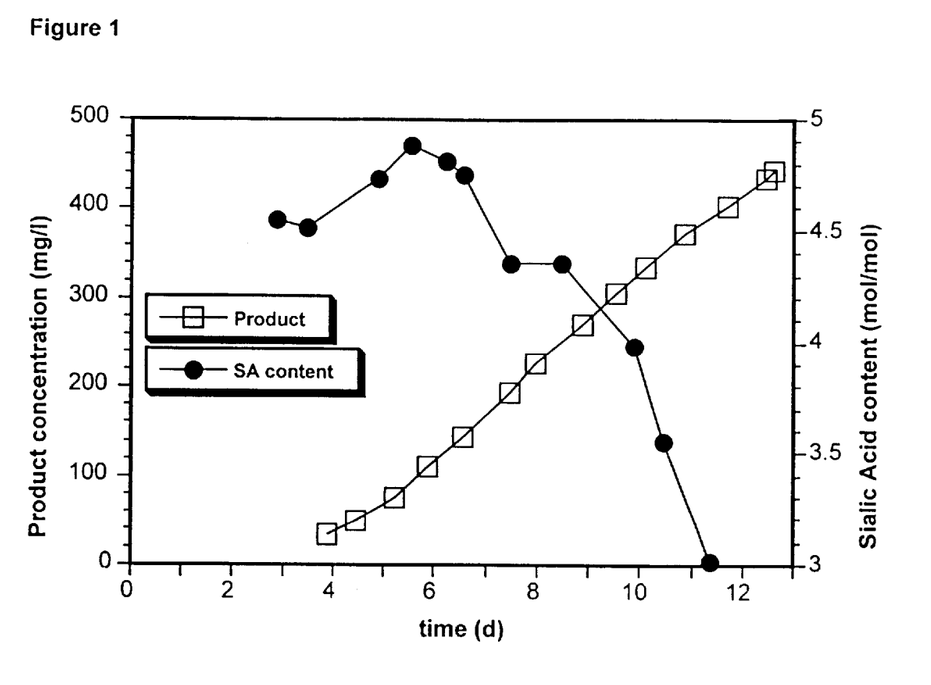
FIG. 1 shows the accumulation of a glycoprotein (TNFR1-IgG1) in cell culture fluid (□) and the sialic acid (SA) content(●) of TNFR1-IgG1 in a representative culture without copper. CHO cells expressing TNFR1-IgG1 were grown under optimal growth conditions for 2 days. On the second day the temperature was reduced to 33° C. and a complex feed mixture was added to the culture consisting of concentrated media components and peptone. As can be seen, the sialic acid content of the glycoprotein produced decreases steadily after about the sixth day in culture whereas the culture is productive for up to 13 days.
Figure 2:
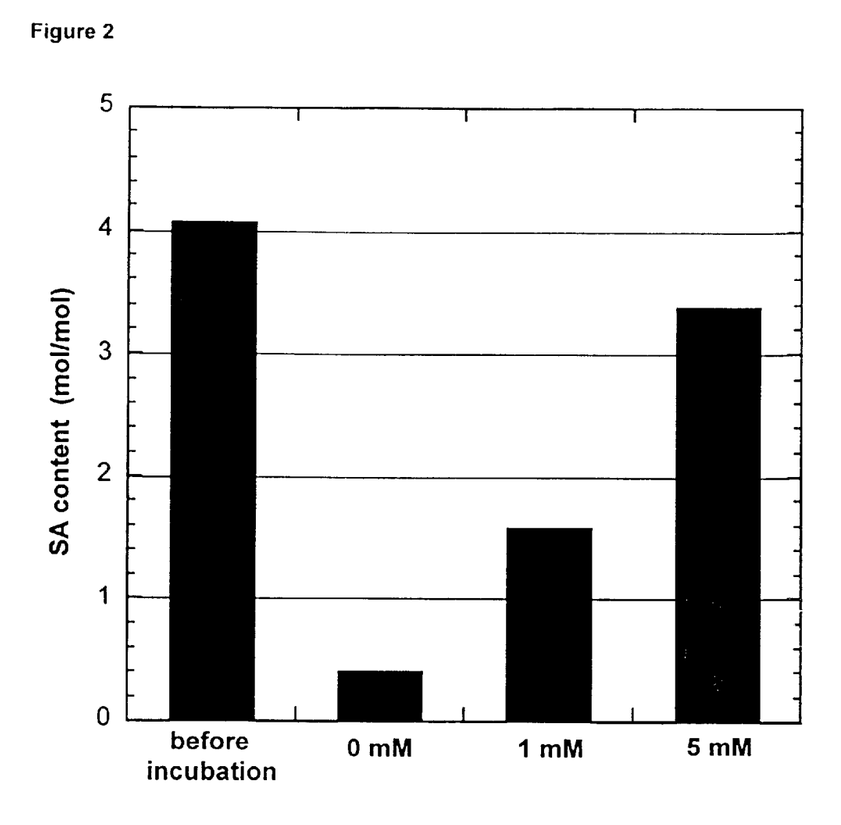
FIG. 2: Sialic acid (SA) content :of TNFR1-IgG1 after incubation of cell culture suspension taken from a perfusion culture at high cell concentration (6% packed cell volume, 77% viability at start of incubation) compared to starting sialic acid content before incubation. A sample of the perfusion culture was removed and incubated in spinner flasks containing 0, 1 mM and 5 mM $CuCl_2$ for 24 hours at 33° C. All cultures died due to oxygen starvation during the incubation period but the copper was effective in stabilizing the SA content in a dose dependent manner.

A representative run at 1000 L scale is shown in FIG. 1. FIG. 1 reports the product concentration as well as the loss of sialic acid over time. As can be seen from FIG. 1 and Table I above, there is significant increase in the amount of glycoprotein produced after about the fifth day of culture. The productivity in mg/l of the glycoprotein produced continues to increase through the twelfth day of culture.

As can be seen from FIG. 1, the sialic acid content of the glycoprotein produced decrease steadily after about the sixth day in culture.

Example II

To test the effect of $CuCl_2$ on stabilization of the sialic acid content high cell concentration from a perfusion culture were incubated over night in spinner flasks with the addition 0, 1 and 5 mM $CuCl_2$. All cells died due to oxygen starvation but as can be seen from FIG. 2 the copper was effective in stabilizing the sialic acid content in a dose dependent manner.

Example III

Figure 3:
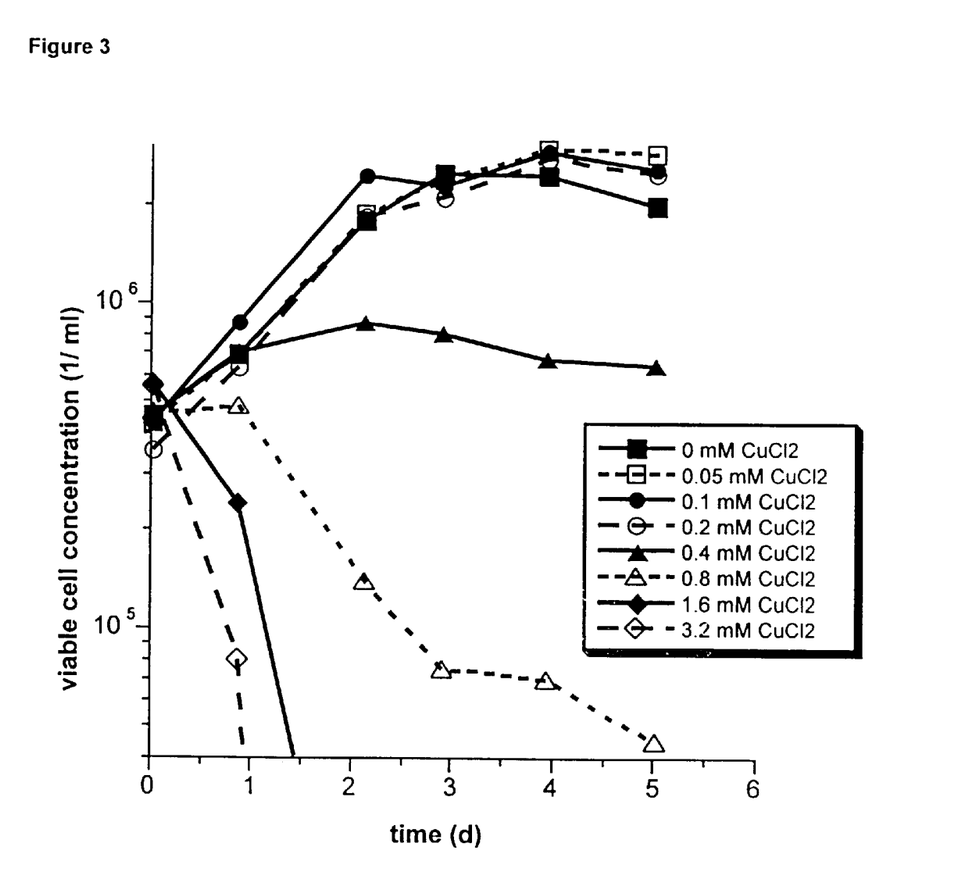
FIG. 3 shows the impact of $CuCl_2$ on growth of CHO cells producing TNFR1-IgG1. $CuCl_2$ was added to the culture medium before inoculation with cells at concentrations from 0 to 3.2 mM. Inhibition of growth could be detected above 0.2 mM.
Figure 4:
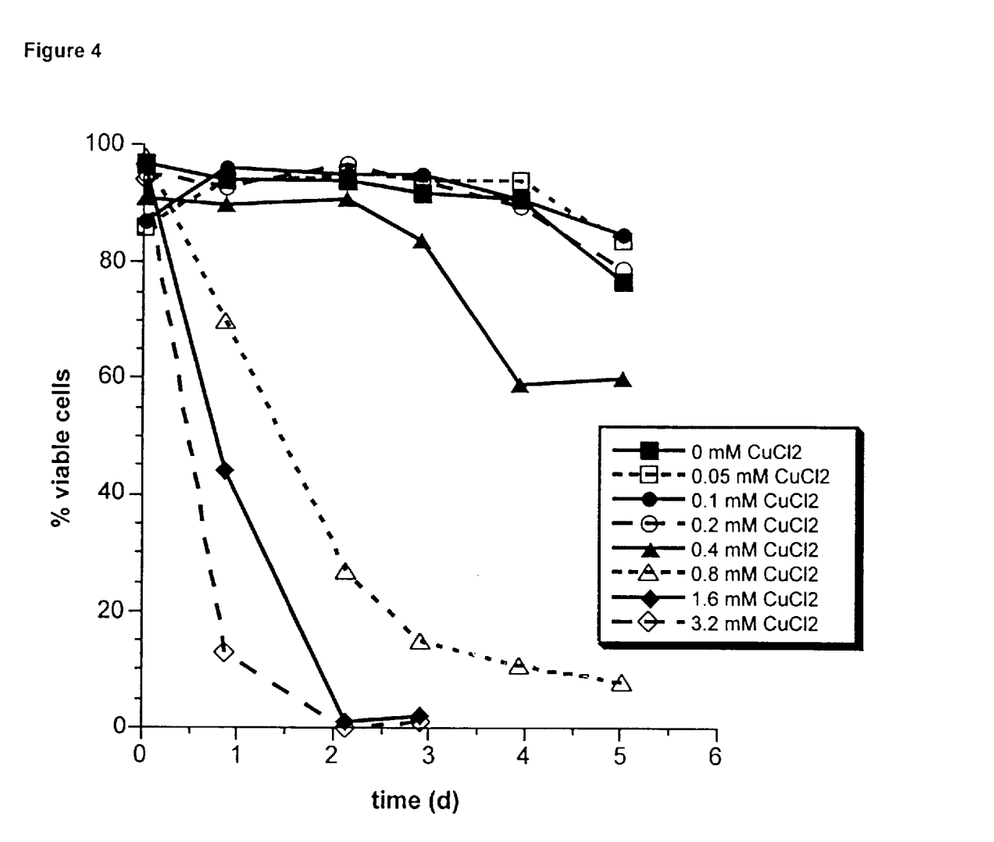
FIG. 4 shows the impact of $CuCl_2$ on viability of CHO cells producing TNFR1-IgG1 under growth conditions. $CuCl_2$ was added to the culture medium before inoculation with cells at concentrations from 0–3.2 mM. A toxic effect could be observed at concentrations above 0.2 mM. Concentrations above 0.4 mM lead to rapid cell death.
Figure 5:
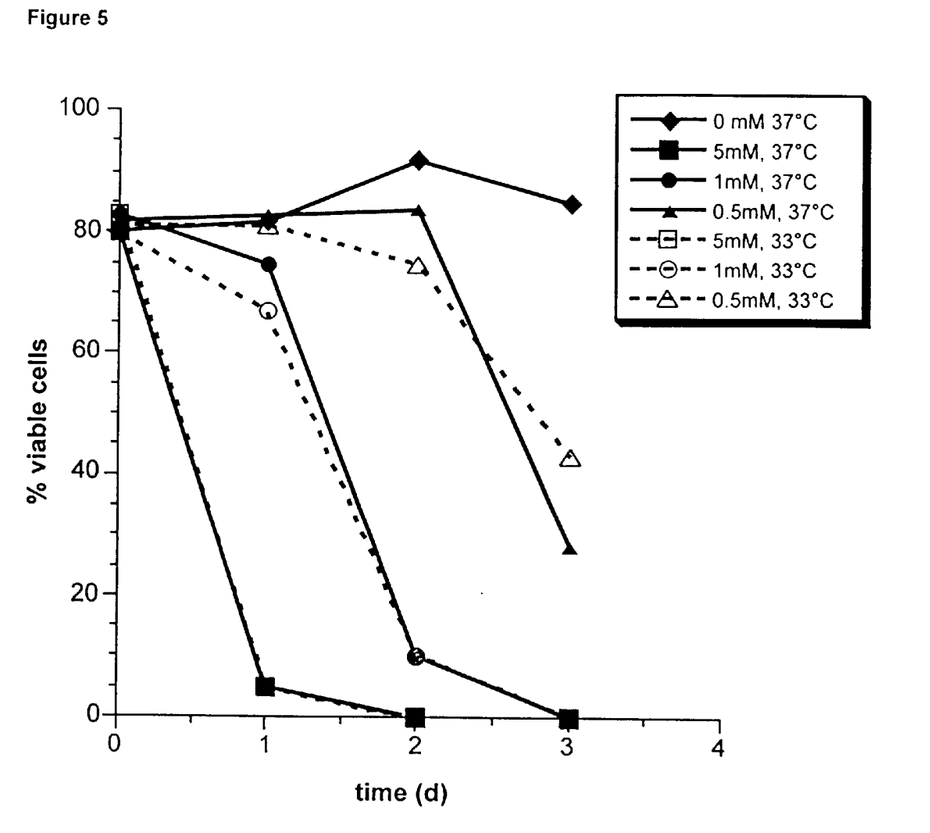
FIG. 5 shows the impact of 0–5 mM $CuCl_2$ on viability of CHO cells producing TNFR1-IgG1 incubated at 37 and 33° C. The toxic effect of $CuCl_2$ was similar for 37 and 33° C.

Since heavy metals such as copper are toxic the effects of $CuCl_2$ concentrations from 0–5 mM on growth and viability of CHO cells at 37° C. and 33° C. incubation temperature producing a glycoprotein were investigated(FIGS. 3, 4 and 5). Toxic effects and growth inhibition could be detected above 0.2 mM $CuCl_2$. The effect was very similar for 37° C. and 33° C. Copper concentrations above 0.4 mM resulted in cell death under conditions normally associated with cell growth.

Example IV

Figure 6:
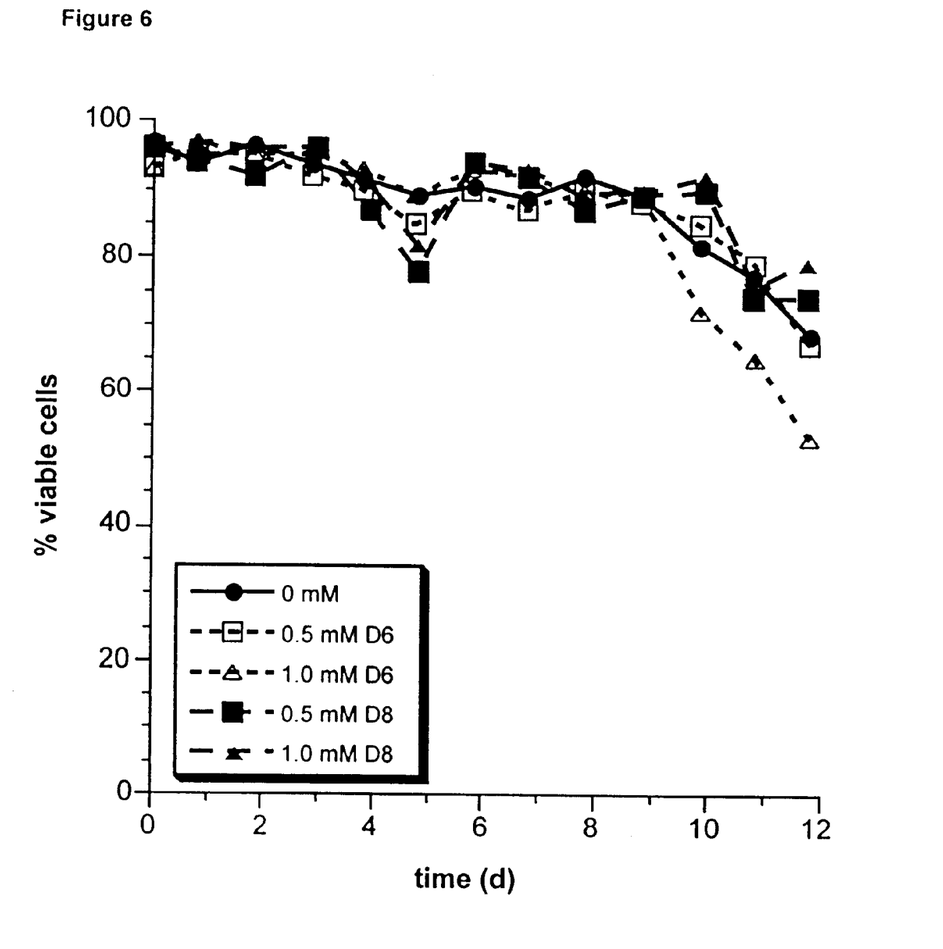
FIG. 6 shows viability profiles of production cultures with 0, 0.5 mM and 1.0 mM $CuCl_2$ added to the cultures on day 6 or 8. The results show that copper can be added to production cultures after a growth phase and during a transition or prior to or during a production phase without detrimental effects on culture viability.
Figure 7:
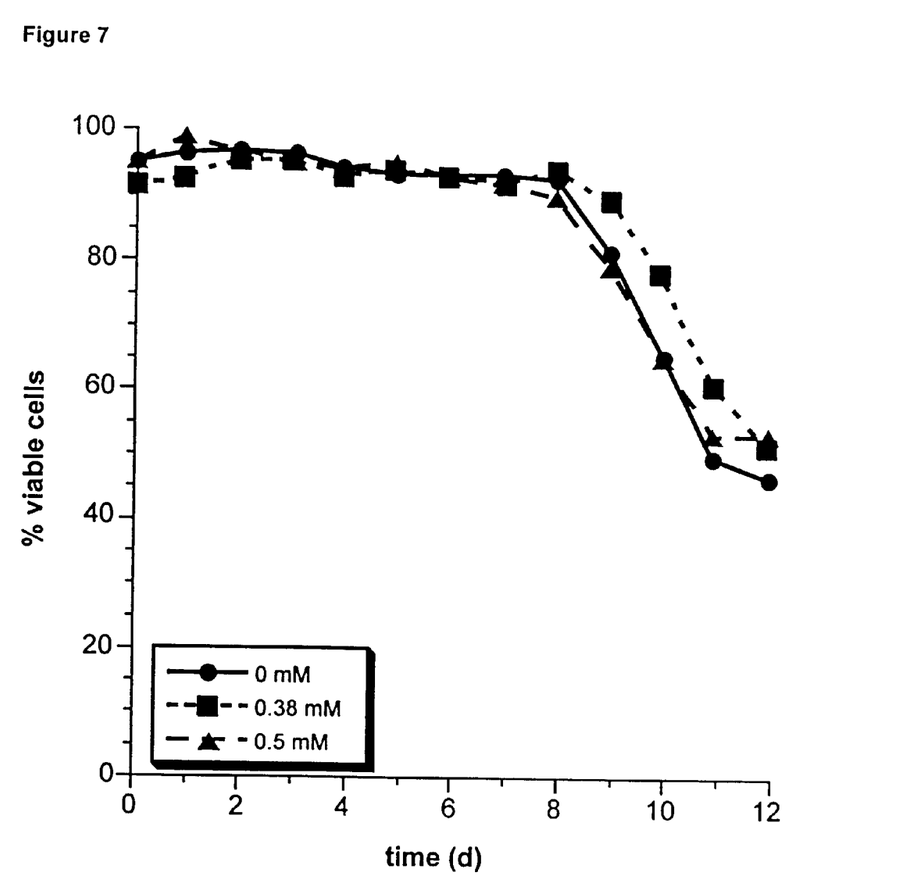
FIG. 7 shows viability profiles of production cultures with 0, 0.38 mM and 0.5 mM $CuCl_2$ added to the cultures on day 6. The results show that a copper concentration of 0.38 mM is not significantly different from 0 and 0.5 mM in terms of viability.

Due to the toxic effects of copper additions higher than 0.2 mM under growth conditions copper additions in the production phase of the glycoprotein production process were investigated. In the process, maximal cell mass was reached after the fifth day in culture. Since significant desialyation occurs after the fifth day in culture and especially significant decrease after about the eighth day in culture (FIG. 1), copper additions of 0.5 and 1.0 mM at day 6 and day 8 of the culture were investigated (FIG. 6).
Results In the first production experiment 0.5 and 1.0 mM $CuCl_2$ was added to the culture. These additions (concentrations which are toxic under growth conditions) did result in good culture performance and productivity. The sialic acid content was stabilized in these cultures as reported in Table II below.

TABLE II

| Culture | Copper amount (mM) | Copper added on day | Sialic Acid content on day 9 (mol/mol) | Product concentr. on day 9 (mg/l) | Sialic Acid content on day 12 (mol/mol) | Product concentr. on day 12 (mg/l) |
|---|---|---|---|---|---|---|
| Control | 0 | — | 4.9 | 227 | 4.3 | 368 |
| $CuCl_2$ | 0.5 | 6 | 5.3 | 230 | 4.9 | 304 |
| $CuCl_2$ | 0.5 | 8 | 5.0 | 244 | 5.0 | 417 |
| $CuCl_2$ | 1.0 | 6 | 5.0 | 218 | 5.0 | 286 |
| $CuCl_2$ | 1.0 | 8 | 5.0 | 289 | 5.0 | 371 |

Example V

Further experiments were run to test copper additions at other concentrations. 0.38 mM copper was added.
Results The results are reported in FIG. 7 and Table III below.

TABLE III

| Culture | Copper amount (mM) | Copper added on day | SA content on day 9 (mol/mol) | Product concentr. on day 9 (mg/l) | SA content on day 12 (mol/mol) | Product concentr. on day 12 (mg/l) |
|---|---|---|---|---|---|---|
| Control | 0 | — | 5.0 | 344 | 3.2 | 543 |
| $CuCl_2$ | 0.5 | 6 | 5.3 | 350 | 5.0 | 545 |
| $CuCl_2$ | 0.38 | 6 | 5.5 | 324 | 4.9 | 518 |

No impact on product quality other than the stabilization of the sialic acid content could be detected.
Results The results clearly show that copper ions can be added to cell culture production processes in a wide range to preserve the oligosaccharide of a glycoprotein.

What is claimed is:

1. A process for producing a glycoprotein by mammalian cell culture, the process comprising:
   culturing a mammalian host cell in a serum free medium in a production phase which is characterized by adding an effective amount of copper ion to the cell culture, said effective amount of copper ion in a concentration effective to minimize the loss of sialic acid on the glycoprotein.

2. The process according to claim 1, wherein the copper ion is added to the cell culture at a concentration of about 0.1 mM to about 2.0 mM.

3. The process according to claim 1 wherein the copper ion is added to the cell culture at a concentration of about 0.1 to about 1.0 mM.

4. The process according to claim 1 wherein the copper ion is added to the cell culture at a concentration of about 0.1 mM to about 0.5 mM.

5. The process according to claim 1 wherein the copper ion is added to the cell culture at a concentration of about 0.3 mM.

6. The process according to claim 1 wherein the production phase is preceded by a growth phase wherein the host cell is cultured under such conditions and for a period of time such that maximum cell growth is achieved.

7. The process according to claim 6 wherein the culture endures for a period of about 9 to about 12 days.

8. The process according to claim 7 wherein the growth phase endures for a period of about between 2 and 5 days.

9. The process according to claim 8 wherein the growth phase endures for a period of about 3 days.

10. The process according to claim 6 wherein the growth phase is followed by a transition phase during which the temperature of the culture is lowered to about between 30° C. and 35° C.

11. The process according to claim 10 wherein the temperature is lowered to about 33° C.

12. The process according to claim 7 wherein copper ion is added on the sixth day of culture.

13. The process according to claim 7 wherein the copper ion is added on the eighth day of culture.

14. The process according to claim 12 wherein the culture endures for a period of about 12 days.

15. The process of claim 1, wherein the host cell is a Chinese hamster ovary cell (CHO).

16. The process according to claim 1, wherein the copper ion is added in the form of copper chloride.

17. The process according to claim 1, wherein the glycoprotein produced is a mammalian glycoprotein.

18. The process according to claim 1, wherein the glycoprotein is a tumor necrosis factor receptor-immunoglobulin chimera.

19. A process for producing a glycoprotein, by mammalian cell culture comprising the steps of;
   (a) culturing a mammalian host cell which expresses a heterologous glycoprotein in a growth phase under such conditions and for a period of time such that maximum cell growth is achieved;
   (b) culturing the host cell in a production phase in a serum free medium which follows the growth phase wherein the cells are cultured in the presence of copper ion at a concentration of about 50 $\mu$M to about 5 mM; and
   (c) recovering the glycoprotein so produced.

20. The process according to claim 19, wherein the mammalian host cell is a CHO cell.

21. The process according to claim 20 wherein the growth phase is followed by a transition phase during which the temperature of the culture is lowered to about between 30° C. and 35° C.

22. The process according to claim 21 wherein the copper ion is added in the form of copper chloride.

23. The process according to claim 22 wherein the glycoprotein produced is a mammalian glycoprotein.

24. A process for producing a glycoprotein by mammalian cell culture, the process comprising:

culturing a mammalian host cell in a serum free medium in a production phase which is characterized by adding an effective amount of copper ion to the cell culture, wherein the copper ion is added to the cell culture at a concentration of about 0.1 mM to about 2.0 mM.

25. The process according to claim 24, wherein the copper ion is added to the cell culture at a concentration of about 0.1 to about 1.0 mM.

26. The process according to claim 24, wherein the copper ion is added to the cell culture at a concentration of about 0.1 mM to about 0.5 mM.

27. The process according to claim 24, wherein the copper ion is added to the cell culture at a concentration of about 0.3 mM.

28. The process according to claim 24, wherein the production phase is preceded by a growth phase wherein the host cell is cultured under such conditions and for a period of time such that maximum cell growth is achieved.

29. The process according to claim 28, wherein the culture endures for a period of about 9 to about 12 days.

30. The process according to claim 29, wherein the growth phase endures for a period of about between 2 and 5 days.

31. The process according to claim 30, wherein the growth phase endures for a period of about 3 days.

32. The process according to claim 28, wherein the growth phase is followed by a transition phase during which the temperature of the culture is lowered to about between 30° C. and 35° C.

33. The process according to claim 32, wherein the temperature is lowered to about 33° C.

34. The process according to claim 29, wherein the copper ion is added on the sixth day of culture.

35. The process according to claim 29, wherein the copper ion is added on the eighth day of culture.

36. The process according to claim 34, wherein the culture endures for a period of about 12 days.

37. The process of claim 24, wherein the host cell is a Chinese hamster ovary cell (CHO).

38. The process according to claim 24, wherein the copper ion is added in the form of copper chloride.

39. The process according to claim 24, wherein the glycoprotein produced is a mammalian glycoprotein.

40. The process according to claim 24, wherein the glycoprotein is a tumor necrosis factor receptor-immunoglobulin chimera.

* * * * *